United States Patent [19]

Dick

[11] Patent Number: 4,694,685
[45] Date of Patent: Sep. 22, 1987

[54] APPARATUS AND METHODS FOR DETERMINING THE WETTABILITY OF VARIOUS SUBSTRATES

[75] Inventor: Franklin A. Dick, Princeton, N.J.

[73] Assignee: Marbetech Corporation, Princeton, N.J.

[21] Appl. No.: 769,443

[22] Filed: Aug. 26, 1985

Related U.S. Application Data

[63] Continuation of Ser. No. 619,549, Jun. 11, 1984, abandoned.

[51] Int. Cl.$^4$ ............................................. G01N 13/00
[52] U.S. Cl. ........................................... 73/104; 73/58; 252/408.1
[58] Field of Search ....................... 252/70, 71, 174.21, 252/174.22, 408.1; 73/104, 866, 58, 60.1; 106/237

[56] References Cited

U.S. PATENT DOCUMENTS

| | | | |
|---|---|---|---|
| 3,537,900 | 11/1970 | Halbert et al. | 252/70 X |
| 3,910,187 | 10/1975 | Cords | 430/302 X |
| 3,928,654 | 12/1975 | Bonnanzio | 252/70 X |
| 3,992,319 | 11/1976 | Alburger | 252/408.1 |
| 4,001,305 | 1/1977 | Dear et al. | 568/50 X |
| 4,045,535 | 8/1977 | Putzer | 528/79 X |
| 4,080,405 | 3/1978 | Agouri et al. | 525/303 X |
| 4,295,976 | 10/1981 | Dessaint et al. | 252/8.9 |
| 4,521,326 | 6/1985 | Seibert et al. | 252/174.21 |
| 4,539,145 | 9/1985 | Alvarez et al. | 252/174.21 X |
| 4,544,495 | 10/1985 | Schmolka | 252/174.21 |
| 4,622,364 | 11/1986 | Ohmori et al. | 525/200 |

Primary Examiner—Tom Noland
Attorney, Agent, or Firm—Arthur L. Plevy

[57] ABSTRACT

There is provided a series of testing formulations or solutions which enable one to determine the critical surface tension or wettability of various solids, semi-solids and viscous liquids by application of the testing solutions to the surfaces of such materials or substrates. The solutions consist of a main solution which is 45 percent purified water and 55 percent of a dihydric alcohol such as ethylene glycol. This basic combination has a wetting tension of 56 dynes and has a completely neutral ph, and a neutral relative polarity. To vary surface tension, a non-ionic surfactant is added in ranges from about 1.5 percent to 0.001 percent by weight of the solution. In this manner the surface tension of each solution is varied in equal or predetermined increments. A dye is also employed to provide good contrast when the solution is placed on a test substrate. The percentage of dye can vary between 0.1 to 1 percent by weight depending upon the particular dye used. Due to the nature of the test solution provided, one can now perform wettability tests on various surfaces which could not be accommodated by prior art techniques. Each of the solutions employed have identical ph, identical viscosity, while further possessing the same neutral relative polarity.

13 Claims, 1 Drawing Figure

U.S. Patent  Sep. 22, 1987  4,694,685
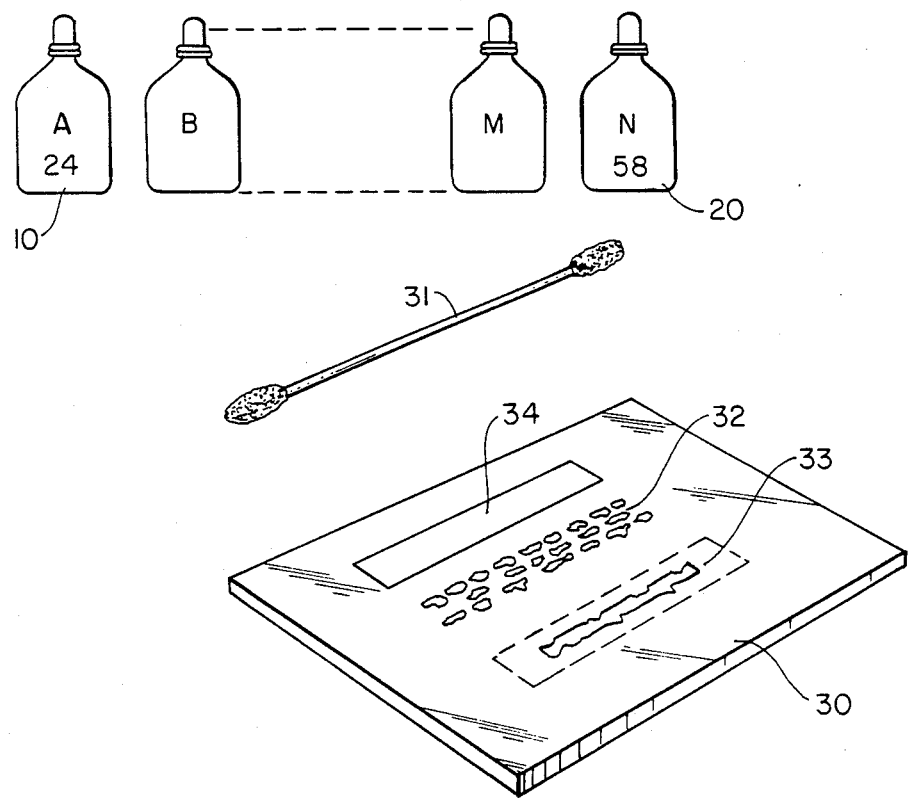

APPARATUS AND METHODS FOR DETERMINING THE WETTABILITY OF VARIOUS SUBSTRATES

This application is a continuation of application Ser. No. 06/619,549 filed on June 11, 1984 and now abandoned.

BACKGROUND OF THE INVENTION

This invention relates to a chemical formulation for determining the wettability of various substrates such as solids, semi-solids, and viscous liquids, and more particularly to a method which includes application of the formulation to a suitable substrate to determine the wettability of the same.

As is known, all matter varies in its ability to wet or to be wetted. This characteristic is inherent with the molecular structure of the substance. The standard unit of measurement is the dyne which by definition is approximately the force that one milligram exerts when under the influence of gravity.

Essentially, certain substances are very difficult to wet such as Teflon. Accordingly, not too many liquids will stick to Teflon, and therefore, it is virtually impossible to print or to paint a Teflon surface. The prior art was cognizant of the general problem of wetting surfaces, and there are many excellent articles as well as texts which describe the mechanics of surface tension and the various parameters which will affect the wettability of different materials.

See for example, an article entitled "How Surface Tension Affects Flexographic Printing" by Franklin A. Dick, the inventor herein, presented at the 1978 FTA Annual Forum, Chicago, May 10, 1978. This article describes the problem inherent in selecting inks to be used in printing and methods to determine that the ink will adequately adhere to the surface to be printed.

To achieve adequate adhesion and smoothness, a coating such as a paint or a printing ink must possess an outer-phase surface tension lower than the critical surface tension of the substrate or surface to which it is being applied. Furthermore, the ultimate critical surface tension of the coating should be lower than that of the substrate if direct molecular bonding is to be achieved. This aspect of surface tension in regard to coating a substrate has been thoroughly investigated in the prior art.

See for example a text entitled CONTACT ANGLE-WETTABILITY AND ADHESION published by the American Chemical Association, R. F. Gould, Editor, 1964, Title 43 of Advances in Chemistry, series 43. Essentially, such texts and other articles describe the problems concerned with applying coatings to surfaces in regard to surface tension and other considerations as well. For example, the wettability of a surface is also a function of the relative polarity of the coating with respect to the substrate. Cognizant of such problems, the prior art has devised various tests and methods to determine wettability. A most popular technique employs the spreading by a swab or a brush of mixed organic solvents of known and various surface tensions.

Mixtures of ethyl cellosolve and dimethyl formamide are commonly used. These solvents are supplied in a kit form, which consists of various bottles, each bottle having a specific surface tension, as for example from 30–56 dynes/centemeter. The user then employs the different liquid to bracket the critical surface tension of the substrate in question. Essentially, if the substrate is wetted by a given liquid, the liquid, when applied to the substrate, will exhibit a uniform pattern. If the liquid cannot wet the substrate, it will retract or otherwise constrict. Accordingly, by using this technique, one can determine the critical surface tension (or the "wetting tension") of the substrate and hence prepare an ink or paint which will adhere to the substrate. Such kits are supplied by various companies, one of which is the Pillar Corporation of Milwaukee. Wis.

The technique as described above is adequate for certain materials such as low density polyethylene. In any event, the system is impractical for measuring any surface which has even a slight degree of solubility in the solvents used. A new solution is formed at the interface which confuses and negates conclusive determination of relative substrate wettability.

Solvent blends also vary in polarity and solvent power. The testing kits as are commercially available, as indicated above, also employ water white, transparent liquids which are difficult to view on various substrates because of lack of visual contrast against the substrate surface. The various solvents are also not stable and cannot be used for monitoring the critical surface tension of various inks, adhesives and paints.

Thus while the apparatus is relatively inexpensive, it has many disadvantages, and therefore, the use of the test kit is extremely limited.

Another technique employed in the prior art serves to establish the contact angle that a droplet of a pure liquid displays when placed on a substrate in question. A device known as a goniometer is employed to establish contact angle and by comparative inference will indicate the relative polarity and critical surface tension of the substrate. This method is fairly precise as compared to the above described technique, but the equipment is not portable, is relatively expensive, and requires technical expertise to obtain reliable data.

The system further suffers in the fact that if migrating additives of substrates are soluble in the testing liquids then the test results can be grossly misleading.

Essentially, as one can ascertain, there is a need for an inexpensive and reliable test for determining the wettability of various substances such as ink, paints and adhesives prior to application of the same to a substrate. It is, therefore, an object of the present invention to provide an inexpensive apparatus which will enable one to establish the relative wettability of various solid and semi-solids.

It is a further object of the present invention to provide a formulation which can be emplaced upon a surface to determine the wettability of the surface which formulation is extremely stable, provides good contrast, and possesses various other characteristics to enable one to more reliably determine the wettability of a surface.

Essentially, as will be described, the apparatus possesses a lower solvent power than prior art systems and also is capable of being colored to provide visual contrast during the test procedure. A major aspect of the formulations to be described is that they possess identical neutral relative polarities and identical ph. The formulations also exhibit the same viscosity and volatility. In this manner many of the disadvantages of the prior art are circumvented and the solutions according to this invention are capable of allowing one to measure surface tension of a much wider variety of substances such as solids, semi-solids and viscous liquids.

BRIEF DESCRIPTION OF THE PREFERRED EMBODIMENT

A solution for use in testing the wettability of various substrates comprising a main blend consisting essentially of a dihydric alcohol and purified water in amounts to provide a surface tension of 56 dynes per centimeter.

BRIEF DESCRIPTION OF THE SOLE FIGURE

The sole FIGURE is a diagram depicting the use of test solutions according to this invention.

DETAILED DESCRIPTION OF THE INVENTION

The formulations according to this invention consist of a mixture of compounds which will enable one to test the relative wettability of various substrates by applying such compounds to the surface of the substrate by means of a swab, brush, droplet or metering bar.

Accordingly, the method of applying the substrates is similar to the method utilized in the prior art and as described above.

The formulations to be described do not have the disadvantages as indicated above, as will be further explained. The formulations are particularly adaptable for application to polyamides, polyurethanes and other medium and high molecular weight organic compounds. They are also applicable to metals and elastomeric blends. The application of such solutions or formulations to substrates to be tested will enable one to perform a rapid determination of the suitability of printing ink, coatings, paints, adhesives, printing press compounds and various other products.

The test solutions according to this invention are composed of a blend of properly purified water such as distilled water containing little impurities and having a ph of 7. The distilled water is blended with a weak dihydric alcohol such as ethylene glycol and non-ionic surfactant. The formulation also contains an appropriate colorant such as a good contrast dye and a ph buffer, if necessary. Preferably, the formulation consists of a mixture of purified water and ethylene glycol. A formulation of 45 percent water and 55 percent ethylene glycol will provide a surface tension of 56 dynes. In this formulation both the water and the ethylene glycol provide equal parameters such as alpha and beta where the square of each parameter is used to determine the wetting tension for the substrate. This technique is well known.

Based on this relationship and these percentages, one now can provide a series of test liquids each of which has 45 percent purified water and 55 percent ethylene glycol plus a surfactant which is employed to change the surface tension and a colorant as a dye which is used to enable visual inspection on the substrate. In this manner, one can achieve a series of test solutions which exhibit surface tensions in the range of 24 to 56 dynes wherein the surface tension between each solution can vary by 1 or 2 dynes over the range. In order to change the surface tension, one will vary the amount of surfactant. The surfactant selected is essentially a non-ionic surfactant. The addition of a non-ionic surfactant to the constant solution blend, as indicated, will produce a formulation of a neutral ph. An example of a suitable non-ionic surfactant is supplied by the Air Products Company of Pennsylvania and sold under the trade name of SURFYNYL 400 SERIES. Suitable compounds are sold under the grade marks 440, 465 and 485. The surfactant is made by reacting ethylene oxide with an acetylene-glycol 2, 4, 9 - tetra-methyl-t-decyne-4, 7-diol.

There are, of course, many non-ionic surfactants that are also suitable and can be employed. The major aspect is that they should not affect the viscosity of the solution blend or the relative ph. In order to obtain a series of solutions each having a surface tension within the range of 24–56 dynes, surfactant is added to the solution blend of 45 percent water and 55 percent ethylene glycol in the following amounts.

For a surface tension of 56 dynes, there is no surfactant added, while for a surface tension of 24 dynes, approximately 1.5 percent of the total weight of the solvent blend is added. From this low value, the amount of surfactant is decreased accordingly to obtain surface tensions of increasing magnitude which solutions may vary one from the other by one or two dynes or any other convenient number desired. Hence one may obtain a series of formulations, as for example, which have surface tensions of 24, 26, 28 ... 56 dynes or 24, 25, 26, 27 ... 56 dynes.

To this solution is added a small percentage of dye which by weight is approximately 0.1–1 percent of the weight of the solvent solution. Ethylene glycol is a good solvent and hence the dyes utilized are selected so that they provide acceptable visual contrast as well as maintaining a neutral ph to the final solution with buffering. Examples of suitable dyes are Victoria Blue B, having a color index number of 729; Methyl Violet, having a color index of 680; Rhodamin B, having a color index of 749; Methylene Blue, having a color index of 922.

As above indicated, the basic solution consists of 45 percent purified water and 55 percent ethylene glycol. This is the main solvent.

The combination indicated above has a surface tension of 56 dynes. A non-ionic surfactant is then added to vary the surface tension and the surfactant range varies between 0.001 percent for the highest surface tension to 1.5 percent for the lowest surface tension. To this formulation is added a dye, as indicated above, which is employed in a concentration between 0.1 to 1 percent depending upon the dye and the color to be obtained.

While the above combination for the basic solvent is preferable, it is understood that other organic solvents may be substituted for the dihydric alcohol as long as neutral polarity is maintained. Various buffers may also be added to assure that the final ph is neutral.

Essentially, the above techniques enable one to provide a series of testing liquids which can be applied to various substances to determine wettability. The testing liquids, as described, have extremely low solvent power, possess a dye for enabling one to visualize the wettability of a surface by the contrast afforded by the dye. Each of the test solutions further possess identical neutral relative polarity, identical ph, similar solubility parameter and degree of hydrogen bonding. The solutions are also of relatively the same viscosity and volatility, and hence the solutions can be used to test the wettability of a wide host of substances which could not be tested by prior art solutions.

In regard to the above reference is made to the sole FIGURE to give one a clearer understanding of how the various solutions are used to determine wettability of a surface. Shown in the FIGURE are various bottles as 10 to 20 designated as A to N.

These bottle contain solutions according to this invention with a different amount of surfactant to achieve a plurality of surface tensions within the range specified. Thus as indicated, bottle 10 would have a surface tension of 24, the next bottle would have a surface tension of 26 and the last bottle 20, the surface tension of 56. These tensions are all expressed in dynes/centimeter.

Shown in the FIGURE is a substrate 30 which may consist of metal, a semiconductor or a viscous liquid or may have a painted surface and so on. The user then takes a cotton swab 31 such as a Q-tip or some other metering device. He will then access a bottle and apply a portion of the liquid on the surface. If the liquid cannot wet the surface, it will retract forming tiny droplets on the surface as indicated by the reference numeral 32 which means that the liquid is entirely unsuitable for wetting the surface. He will then go to another bottle and repeat the test. If the liquid partially wets the surface as shown in 33, then the original width and length of the applied liquid stripe will be reduced substantially in area whereas the liquid will gather together, as indicated by reference numeral 33. If the liquid wets the surface as indicated by reference numeral 34, then the original applied pattern will remain as a stripe or retain the same size and shape as the pattern impressed by the use of the Q-tip 31. This indicates that the liquid can wet the surface properly. Thus the user now has a knowledge of the wetting tension of the substrate and prepares paint, adhesive and various other substances such as inks which will adhere and firmly bond to the surface based on having a compatible surface tension.

As one can ascertain, each bottle will contain a solution of different tension which various bottles may be included in a kit together with swabs so that such tests can be performed.

I claim:

1. In a process for use in testing the wettability of various substrates by wiping the substrate with a solution and viewing the wiped substrate to determine whether the solution properly wets the substrate or retracts on the substrate the improvement therewith of using a solution, comprising:
   a main blend consisting of a dihydric alcohol and purified water in amounts to provide a surface tension of 56 dynes per centimeter.

2. The solution according to claim 1, wherein said main blend consists of 55 percent of a dihydric alcohol—namely, ethylene glycol and 45 percent of purified water.

3. The solution according to claim 1, further including a small amount of a dye to provide visual contrast.

4. The solution according to claim 3, wherein the amount of said dye is between 0.1 to 1 percent of the weight of said main blend.

5. The solution according to claim 4, wherein said dye is selected from one of the following groups, Victoria Blue B, Methyl Violet, Rhodamine B, Methylene Blue.

6. In a process for use in testing the wettability of various substrates by wetting the substrate with a solution and viewing the wetted substrate to determine whether the solution properly spreads on the substrate or retracts on the substrate, the improvement therewith of using a solution, comprising:
   a main blend consisting of 55 percent by volume of a dihydric alcohol and 45 percent by volume of purified water, a non-ionic surfactant added to said main blend in the range of 0.001 to 1.5 percent by weight of said blend to provide solutions having a surface tension in the range of 24 to 56 dynes per centimeter.

7. The solution according to claim 6, wherein said dihydric alcohol is ethylene glycol.

8. The solution to claim 6, further including a small amount of a dye to provide visual contrast.

9. The solution according to claim 8, wherein the amount of said dye is between 0.1 percent of the weight of said blend.

10. The solution according to claim 9, wherein said dye is selected from one of the following groups, Victoria Blue, Methyl Violet, Rhodamine B, Methylene Blue.

11. The solution according to claim 6, wherein said purified water is a distilled water.

12. In a process for use in testing the wettability of various substrates by wetting the substrate with a solution and viewing the wetted substrate to determine whether the solution properly spreads on the substrate or retracts on the substrate, the improvement therewith of using a solution, comprising:
    a main blend consisting of 55 percent in volume of ethylene glycol and 45 percent in volume of purified water, a non-ionic surfactant added to said main blend in a range of 0.001 to 1.5 percent by weight of said blend to provide solutions having surface tensions in the range of 24 to 56 dynes per centimeter and a dye added to said solution in the range of 0.1 to 1 percent by weight of said blend to provide visual contrast when said solution is applied to the surface of a substrate to be tested for wettability.

13. The solution according to claim 12, wherein said dye is selected from the group consisting of Victoria Blue B, Methyl Violet, Rhodamine B, Methylene Blue.

* * * * *